United States Patent
Siegel

(10) Patent No.: US 7,968,113 B2
(45) Date of Patent: Jun. 28, 2011

(54) LIQUID BANDAGES

(75) Inventor: Gregg Siegel, San Antonio, TX (US)

(73) Assignee: Biomedical Development Corp., San Antonio, TX (US)

( * ) Notice: Subject to any disclaimer, the term of this patent is extended or adjusted under 35 U.S.C. 154(b) by 210 days.

(21) Appl. No.: 12/011,879

(22) Filed: Jan. 30, 2008

(65) Prior Publication Data

US 2009/0192475 A1    Jul. 30, 2009

(51) Int. Cl.
*A61F 13/00*    (2006.01)

(52) U.S. Cl. ............... 424/443; 424/486; 424/78.02; 424/78.35; 514/772.1

(58) Field of Classification Search .............. None
See application file for complete search history.

(56) References Cited

U.S. PATENT DOCUMENTS 6,139,856 A * 10/2000 Kaminska et al. ............ 424/404
6,537,577 B1 * 3/2003 Siegel ........................... 424/486

* cited by examiner

*Primary Examiner* — Robert A Wax
*Assistant Examiner* — Hasan A Ahmed
(74) *Attorney, Agent, or Firm* — John Lezdey & Assoc

(57) ABSTRACT

A method is provided to treat skin to restore barrier homeostasis and to promote normal stratum corneum function by applying to the skin a liquid composition which forms a phase inversion membrane. The amount of solids in the liquid composition is varied so as to provide a desired degree of porosity to the resulting membrane.

7 Claims, No Drawings

LIQUID BANDAGES

The U.S. government owns certain rights in the present invention pursuant to grant SBIR#R43AR052213 from the National Institutes of Health.

FIELD OF THE INVENTION

The present invention relates to the treatment of skin and skin eruptions utilizing a polyvinylidene fluoride based film forming composition with specific moisture vapor transmission rate (MVTR) for the various skin conditions to provide a synergistic effect with a medicament being utilized.

BACKGROUND OF THE INVENTION

Polymeric coatings have been used to deliver drugs systemically and as topical bandages. Polyvinylidene fluoride has been found to provide compositions which have microporosity and breathability. The problems arise to formulate a coating which also has good adherence to skin or animal furs and still provide a moisture vapor transmission that is suitable for its intended use and will deliver a drug at a desired rate and/or penetrate the stratum corneum to a controlled degree.

U.S. Pat. No. 6,139,856 to Kaminska et al, which is herewith incorporated by reference, discloses polyvinylidene fluoride-based compositions which provide fluid resistant barrier films with good durability and skin-adhesion properties. However, there is included in the film formation amine-substituted acrylic polymers and dialkyl acrylates which results in a pore shape and MTVR that is not suitable to control the degree of penetration and varying of MTVR with the type of medicament utilized.

U.S. Pat. No. 5,041,287 to Driggers, which is herein incorporated by reference, relates to spray-on bandages and gloves which comprise PVDF, an aqueous emulsion of acrylates and methacrylates, an unsaturated carboxylic acid and/or acrylamide, and a plasticizer.

PVDF is a mechanically tough thermoplastic that is readily and stably polymerized without stabilizers or low molecular weight contaminants. It is sold by Ausimont USA, Thorofare, N.J. under the trademark HYLAR®. However, HYLAR is usually combined with acrylic resins such as RHOPLEX® of Rohm and Haas Corp., Philadelphia, Pa.

Silicone sheeting has been used for treating hypertrophic scars and keloids. It has been hypothesized that efficacy is the result of hydration and occlusion, although hypertonic scars and keloids exhibit greater hydration than normal skin. The problem in using silicone is that patients have exhibited discomfort, itching, development of rashes and perceived lack of benefit. Therefore, a substitute for silicone sheeting is desirable.

Dermatitis and eczema are often used synonymously to describe a polymorphic pattern of inflammation in which the acute phase is characterized by erythema, vesiculation, dryness and lichenification. Topical treatments have been focused on occlusive or semi-occlusive dressings and lipids to promote normalization of the skin.

Keratinization and other conditions that involve dry and scaly skin have a defective barrier function and an elevated transepidermal water loss which worsens in the winter that does not have a universal treatment to improve conditions and restore barrier homeostasis.

SUMMARY OF THE INVENTION

The present invention relates to liquid bandages and coating compositions for treating problem skin that can achieve distinct physical coating characteristics through component variation. More particularly, there is provided a method of treating the skin with the coating composition alone or by incorporating a medicament and adjusting the composition to provide a desired moisture vapor transmission rate (MVTR) for use with a specific skin condition or a specific skin treating medicament.

Accordingly there is provided a method of treating skin to restore barrier homeostasis and to promote normal stratum corneum function by administering to the site of problem of the skin a composition comprising;
  a) a solids content of about 5 to 20% by weight, said solids comprising an acrylic resin and polyvinylidene difluoride or a copolymer thereof in a ratio of about 1:4 to 1:2;
  b) about 1 to 11% by weight of water,
  c) acetone, and
  d) optionally up to about 5% by weight of a medicament,
    with the proviso that the acrylic resin is in the form of an aqueous emulsion and the emulsion is adjusted as to vary the acrylic resin content and the porosity of the resultant phase inversion membrane.

Preferably the resultant film for use with a medicament in a ratio of 2:1 is of PVDF to acrylic acid in the emulsion. The solids content is varied so as to control the degree of porosity in the resulting film.

The film formed with a high range of solids is suitable when the film alone is used alone to restore skin barrier homeostasis and provides an occlusive bandage with a degree of porosity to allow for perspiration.

It is therefore an object of the invention to provide a composition to protect the skin and improve barrier homeostasis of the skin.

It is another object of the invention to provide a coating to release biologically active agents to treat the skin.

It is a further object of the invention which can provide a composition which can be varied as to porosity and MVTR.

It is yet another object to provide a composition which can improve skin barrier homeostasis without any medicaments.

It is yet a further object of the invention to provide a coating having an MVTR between 20 and 220 $g/m^2/24$ hrs.

DESCRIPTION OF THE PREFERRED EMBODIMENTS

The present invention relates to a method for treating skin to restore barrier homeostasis and to promote normal stratum corneum function by applying to the problem skin a liquid coating composition comprising:
a) about 5 to 35% by weight of solids of an acrylic resin and polyvinylidene difluoride or a copolymer thereof in a ratio of about 1:4 to 1:2;
b) about 1 to 11% by weight of water,
c) acetone, and optionally
d) up to about 5% of a medicament,
  with the proviso that the acrylic resin is in the form of an aqueous emulsion and the emulsion is formed by varying the solids content whereby the degree of porosity of the resultant phase inversion membrane formed is controlled by the concentration of solids and the moisture vapor transmission rate is between 20 and 220 $g/m^2/24$ hrs.

In the treatment of skin with the bandages of the invention it is necessary that the bandage have a MTVR of greater than 20 $g/m^2/24$ hrs to allow for the escape of moisture from perspiration so that the formed film adheres to the skin for an extended period of time.

When the solids content is greater than 35% w/w the composition is not fluid and a film will not form. Preferably the solids content is about 5.0 to 20% w/w with the lower content having the greatest porosity. The higher the solids content, the thicker the film which is formed.

For the treatment of scars a film containing a solids content of about 10 to 20% w/w is suitable with a ratio of polyvinylidene difluoride to acrylic resin of about 2:1.

The coatings formed by the present invention are utilized as vehicles for medicaments and other agents which are intended to treat a skin area on contact. The coatings can act as a delivery system or carrier for medicaments which are soluble in the solvent. The thickness of the coatings is preferably about 20-60 μm, preferably 40 μm.

Other medicaments or other skin treating agents can be added to the coating composition in an amount of about 0.1 to 10% by weight based on their intended use or applied separately and then coated over. Usually about 5% by weight is sufficient for treatment of many skin conditions.

The film forming composition of the invention can be formed utilizing a polyvinylidene difluoride homopolymer and/or copolymer thereof. However, the amount of the copolymer utilized should not be an amount which will effect the characteristics of the polyvinylidene difluoride.

Useful acrylic resins are lower alkyl acrylates and methacrylates having 1 to 8 carbon atoms in the alkyl group such as methyl acrylate, ethyl acrylate, isopropyl acrylate, methyl methacrylate, propyl methacrylate, ethoxyethyl methacrylate, acrylamide, methacrylamide, N-alkyl substituted acrylamides and methacrylamides such a N-methyl methacrylamide and N-isopropyl methacrylamide and N-vinyl pyrolidone. Also polymers of the alkyl acrylates and methacrylates with 30-50% hydroxyl ethyl and hydroxyl propyl acrylates and methacrylates are included in this category.

In addition to the acrylic monomer and methacrylic monomer mixtures set forth above to prepare polymers there can be added to the monomer or monomer mixture acrylic acid, methacrylic acid, itaconic acid, maleic acid and fumaric acid.

Preferred alkyl acrylates which can be used to prepare the acrylic polymer dispersant are ethyl acrylate, propyl acrylate, isopropyl acrylate, butyl acrylate, tertiary butyl acrylate, pentyl acrylate, hexyl acrylate, octyl acrylate, nonyl acrylate, decyl acrylate, laurel acrylate, and the like.

The compositions can be applied by spraying, painting or rolling onto the infected area.

To prepare the composition of the invention to be used with the medicaments, it is advantageous to prepare an aqueous emulsion of the acrylic compounds prior to admixture with the polyvinylidene difluoride.

Preferred acrylic polymer dispersants include the following:
1. methyl methacrylate, butyl acrylate and acrylic acid
2. isodecyl methacrylate, butyl acrylate and acrylic acid
3. stearyl methacrylate, butyl acrylate and acrylic acid
4. methyl methacrylate, 2-ethylhexyl acrylate and methacrylic acid It may be desirable to neutralize the acrylic dispersion so as to make it more compatible for use on the skin or to incorporate the medicament.

Typical basic compounds that can be used to neutralize the acrylic polymer dispersant or to adjust the pH of an aqueous dispersion of the polymer dispersant to a pH of about 7 are as follows: ammonium hydroxide, amines, such as primary amines, secondary amines, hydroxyl amines, typical of these amines are diethanolamine, triethanolamine, N-methylethanolamine, N-aminoethanolamine, N-methyldiethanolamine, monoisopropanolamine, diisopropanolamine, triisopropanolamine, hydroxyalkylamine, butanolamine, hexanolamine, methyldiethanolamine, N,N-dioctylaminoethylamine, ethylenediamine, diethylenetriamine, triethylamine, and the like.

Example 1

Objective: The purpose of this study was to evaluate PVDF/acrylic coatings as a treatment of keratosis pilaris (KP) in a 12-week clinical trial. The coating can be used for local drug delivery of a variety of active compounds including salicylic acid, which was used for this study at a 2.0% concentration.

The coating formula utilized was 5.08% Rhoplex B-15R®, which contained 54% water, 10.16% Hylar SN®, 12.5% total solids and 84.76% acetone.

Methods: The study was designed as a double-blind, randomized left/right comparison to evaluate the efficacy of a polymer-based skin coating with or without salicylic acid to treat KP. Over a 12-week period, subjects with bilateral keratosis pilaris applied the polymer coating to one arm and the polymer coating containing salicylic acid to the contralateral arm. Thirty subjects have bilateral KP were enrolled in the study and treatment was randomized by left/right assignment. Measurements and subjective evaluation by the participants were completed at baseline and weeks 2, 4, 8, and 12. Parameters for KP evaluation included scale and roughness, clinical impression of treatment response, and subject impression of treatment response.

Analysis: The Signed-Ranks test was used to assess changes in ordinal and interval variables; the Student T test was used to assess differences in continuous variables. The Friedman test was used to compare ordinal repeated measures. Significance was ascribed to a p value $\leq 0.05$.

Results: Twenty-two subjects completed the study and were considered evaluable. Both treatments demonstrated significant improvement ($p<0.008$) with regard to scale and roughness, and clinical evaluation of treatment ($p<0.0001$). With regard to physician and subject impression of treatment, moderate and marked improvement was observed over time. Of note, there were 19 study sites (arms) that presented with either moderate or severe ratings for scale and roughness at baseline. By week 12, all but 3 of the sites had only either slight or no scale and roughness.

Example 2

Objective: The purpose of this study was to evaluate PVDF/acrylic coatings as a treatment for mature hypertrophic scars and keloids in a 16-week clinical trial. The primary efficacy endpoint was the Vancouver Scar Scale (VSS), Study participants also provided self-assessment of itching. The coating formula utilized was 6.1% Rhoplex B-15R®, which contained 54% water, 12.2% Hylar SN®, 15.0% total solids and 81.7% acetone.

Methods: Forty volunteers having a mature (>7 months old) keloid or hypertrophic scar met inclusion/exclusion criteria and were randomized to either silicone sheeting or polymer coating treatment groups. Study participants self-administered the polymer coating treatment twice daily for the duration of the 16-week study period, and those randomized to the silicone sheeting group used the product consistent with instructions from the manufacturer. Scar measurements and subjective evaluation by the participants were completed at baseline and weeks 4, 8, and 16. The Vancouver Scar Scale, which provides a composite score for vascularity, pliability, and height, and an ordinal score for pigmentation. was used to assess scars. Study participants also provided self-assessment of itching using a 0-3 scale.

Analysis: A repeated measures (pre-treatment/post-treatment) design was used for within and between group comparisons, with time as the group variable. Wilcoxon Signed Rank Test and the Mann-Whitney U Test were used to explore within and between group comparisons where appropriate. Significance was ascribed to a p value $\leq 0.05$.

Results: Seventeen subjects completed the study and were considered evaluable. Subjects treated with the PVDF/acrylic coating showed a statistically significant difference in VSS index score from baseline at weeks 4 ($p<0.006$), 8 ($p<0.001$) and 16 ($p<0.0001$), demonstrating progressive improvement over the study period. Changes in scar pigmentation approached significance at week 4 ($p<0.083$) and continued treatment led to significant differences observed at week 16 ($p<0.009$). Significant and progressive improvement in itching sensation was reported at weeks 4 ($p<0.034$), 8 ($p<0.017$) and 16 ($p<0.003$). Notably, all individuals reported some degree of relief, with those reporting "no itching" increasing from 17.6% at baseline to 58.8% at the end of the study.

Example 3

Range of Formulations to Form Phase-Inversion Membranes Necessary to Treat Skin

Successful coating formulations have been developed using film-forming components over a broad range of proportions. Typically, an acrylic emulsion is combined with the PVDF copolymer and dissolved in acetone for application to the skin. This acrylic is an aqueous emulsion that provides microporosity through the phase inversion process (as described below), and contributes to adhesivity. The porosity imparts a semi-occlusive character to the coating. Additional acrylics may be added to the formulation as well.

Phase-inversion membranes are solvent-cast structures in which two liquid phases form to produce a stabilized gel prior to complete solvent depletion. In the present case, as the acetone evaporates, the relative proportion of the less volatile, nonsolvent component (i.e., water—from the acrylic emulsion) increases and eventually causes the polymer to separate into a polymer-rich continuous phase containing an acetone-rich dispersed phase. Films that form under these circumstances have a microporous structure.

The microporosity of PVDF coatings serves multiple purposes. Microporosity allows the skin underneath the coating to respire and does not completely impede transepidermal water loss. This in turn promotes coating adhesion to skin by preventing moisture buildup from perspiration that could potentially loosen coatings. Without a microporous structure, it is likely that sweat retention would occur under the coating and cause lift and separation from the skin. Likewise, the coating aids in restoring skin barrier homeostasis by providing a covering that partially retards transepidermal water loss. In addition, microporosity can be used to create a porous binder for the inclusion and sustained release of drugs.

Although many combinations of the components can be formulated to produce suitable coatings, preferred formulations consist of Hylar S/N PVDF copolymer and Rhoplex B15R acrylic emulsion in a 2:1 ratio, dissolved in acetone. The PVDF and acrylic components comprise the solids content of the dried film after the acetone has evaporated. Rhoplex B-15R is an acrylic emulsion containing approximately 54% water. This water content is taken into account when calculating the solids concentration of formulations.

The upper range for solids content is approximately 35% w/w. Formulations with solids content in excess of 35% w/w are not fluid, and will not form films. Preferred formulations have solids contents between 5.0%-20%, often comprised of 8.65% or 12.5% w/w. Adjusting the solids content will have a direct effect on the thickness of the dried coating, with higher solids content formulations providing thicker films. This will also have an effect on the occlusivity of the formulations. In addition, by varying the amount of the acrylic emulsion in the formulation, the microporosity of the film can be widely adjusted (Table 1)

TABLE 1

Formulations of PVDF/Acrylic Coatings

| Component | Formula 1 5.5% solids | Formula 2 8.65% solids (high emulsion) | Formula 3 8.65% solids (mid emulsion) | Formula 4 12% solids (mid emulsion) | Formula 5* 8.65% solids (no emulsion) |
|---|---|---|---|---|---|
| Hylar S/N | 4.50% | 5.50% | 7.03% | 9.76% | 8.65% |
| Rhoplex B-15R | 2.25% | 6.86% | 3.52% | 4.88% | 0.00% |
| Acetone | 93.25% | 87.64% | 89.45% | 85.36% | 91.35% |

*Formulations without acrylic emulsion form films but do not adhere to skin for extended periods of time.

B. Moisture vapor transmission rate (MVTR) testing was performed to quantify the amount of porosity and breathability of coatings. Corresponding MVTR for the formulations in Table 1 are shown in Table 2.

TABLE 2

Solids Content, Emulsion Content and Impact on Moisture Vapor Transmission Rate (MVTR)

| Formulation | Solids Content (w/w) | Description | MVTR |
|---|---|---|---|
| Formula 1 | 5.5% | Decreased solids; Mid Emulsion | 222.52 |
| Formula 2 | 8.65% | High Emulsion | 199.69 |
| Formula 3 | 8.65% | Mid Emulsion | 180.90 |
| Formula 4 | 12% | Increased Solids | 157.76 |
| Formula 5 | 8.65% | No emulsion | 148.16 |
| Food Wrap | Food Wrap | Control | 115.95 |

What is claimed is:

1. A method for treating skin of a patient to restore barrier homeostasis and to promote normal stratum corneum function without medicaments which comprises applying to the skin a liquid composition that forms a phase inversion membrane having a moisture vapor transmission rate of greater than 20 g/m$^2$/24 hr which composition comprises a) about 5 to 35% by weight of solids of a neutralized acrylic resin and polyvinylidene difluoride or the copolymers thereof in a ratio of 1:4 to 1:2;
b) about 1 to 11% by weight of water; and
c) acetone;

with the proviso that the acrylic resin is in the form of an aqueous emulsion and the emulsion is formed by varying the amount of solids to arrive at a degree of desired porosity in the resultant membrane.

2. The method of claim 1 wherein the membrane forms an occlusive or semi-occlusive bandage.

3. The method of claim 1 wherein the skin is treated for wrinkles.

4. The method of claim 1 wherein the skin is treated for scars.

5. The method of claim 1 wherein a phase inversion membrane of about 40 μm in thickness is formed.

6. The method of claim 1 wherein the phase inversion membrane forming composition comprises
   a) about 6 to 18% by weight of a polymer selected from the group consisting of polyvinylidene difluoride and the copolymers thereof;
   b) about 1 to 6% by weight of an emulsion of a neutralized acrylic resin selected from the group consisting of acrylic acid, methacrylic acid, alkyl acrylate and alkyl methacrylate;
   c) about 1 to 6% by weight of water; and
   d) acetone.

7. The method of claim 1 wherein the patient is suffering from keratosis pilaris.

* * * * *